United States Patent [19]
Bell et al.

[11] Patent Number: 5,569,789
[45] Date of Patent: Oct. 29, 1996

[54] MULTISTAGE INDIRECT PROPYLENE HYDRATION PROCESS FOR THE PRODUCTION OF DIISOPROPYL ETHER AND ISOPROPANOL

[75] Inventors: Weldon K. Bell, Pennington; Stephen H. Brown, Princeton, both of N.J.; Jeffrey C. Trewella, Kennett Square, Pa.

[73] Assignee: Mobil Oil Corporation, Fairfax, Va.

[21] Appl. No.: 510,371

[22] Filed: Aug. 2, 1995

Related U.S. Application Data

[63] Continuation-in-part of Ser. No. 347,933, Dec. 1, 1994, abandoned.

[51] Int. Cl.$^6$ .......................... C07C 29/00; C07C 31/10; C07C 41/06; C07C 43/04
[52] U.S. Cl. .......................... 568/697; 568/694; 568/897; 568/907
[58] Field of Search .................... 568/694, 697, 568/897, 907

[56] References Cited

U.S. PATENT DOCUMENTS

| | | |
|---|---|---|
| 4,042,633 | 8/1977 | Woods . |
| 4,182,914 | 1/1990 | Imaizumi . |
| 4,579,984 | 4/1986 | Neirw et al. . |
| 4,783,555 | 11/1988 | Atkins . |
| 4,857,664 | 8/1989 | Huang et al. ............... 568/697 |
| 4,886,918 | 12/1989 | Sorensen et al. .......... 568/897 |
| 4,935,552 | 6/1990 | Child et al. ................. 568/697 |
| 5,138,102 | 8/1992 | Beech, Jr. et al. . |
| 5,208,387 | 5/1993 | Harandi et al. ............ 568/697 |
| 5,225,609 | 7/1993 | Bell et al. .................. 568/697 |
| 5,399,788 | 3/1995 | Marker ..................... 568/697 |
| 5,405,814 | 4/1995 | Beech et al. ............... 568/697 |

FOREIGN PATENT DOCUMENTS 323138  12/1988  European Pat. Off. .

*Primary Examiner*—Joseph E. Evans
*Attorney, Agent, or Firm*—Ronald A. Bleeker; Malcolm D. Keen

[57] ABSTRACT

A multistaged fixed catalyst bed process for the production of diisopropyl ether and isopropanol is disclosed comprising a fixed bed of serially connected stages containing zeolite Beta catalyst. A feedstream of propylene and water equivalents selected from the group consisting of water, isopropanol and diisopropyl ether is introduced into each stage at a rate sufficient to provide a mole ratio of water equivalents to propylene equivalents that increases in increments by stage from at least 0.1 in a first stage to at most 1.2 in a final stage. The feedstream is introduced at a temperature between 50° and 450° C., pressure between 700 and 24000 kPa, and weight hourly space velocity between 0.10 and 30, based on catalyst, whereby a single non-aqueous liquid phase is maintained in the fixed bed. An effluent product stream is recovered comprising diisopropyl ether, isopropanol and water from the final stage. Isopropanol is recycled to the first stage when the preferred product is diisopropyl ether. When the preferred product is isopropanol, diisopropyl ether and water are recycled to the first stage.

17 Claims, 3 Drawing Sheets

MULTISTAGE INDIRECT PROPYLENE HYDRATION PROCESS FOR THE PRODUCTION OF DIISOPROPYL ETHER AND ISOPROPANOL

CROSS REFERENCE TO RELATED APPLICATIONS

This application is a continuation-in-part of prior application Ser. No. 08/347,933, filed 1 Dec. 1994, now abandoned.

FIELD OF THE INVENTION

This invention relates to a process for the production of ethers and/or alcohols from light olefins and water. The invention particularly relates to a serially connected, multistage fixed bed process for the production of high octane value diisopropyl ether and isopropyl alcohol by indirect hydration of propylene in a single liquid hydrocarbon phase employing zeolite catalyst. The invention especially relates to a method for promoting indirect propylene hydration and ether formation by the progressively larger interstage injection of oxygenates in the feed to the multistage process.

BACKGROUND OF THE INVENTION

Lower molecular weight alcohols and ethers such as isopropanol (IPA) and diisopropyl ether (DIPE) are in the gasoline boiling range and are known to have high blending octane numbers. In addition, by-product propylene from which IPA and DIPE can be made is usually available in a fuels refinery. An important aspect of research in the petroleum industry relates to processes to produce high octane lower aliphatic alkyl ethers as octane boosters and supplementary fuels.

The catalytic hydration of olefins, particularly $C_3$ and $C_4$ olefins, to provide alcohols and ethers is a well-established art. Representative olefin hydration processes are disclosed in U.S. Pat. Nos. 2,262,913; 2,477,380; 2,797,247; 3,798,097; 2,805,260; 2,830,090; 2,861,045; 2,891,999; 3,006,970; 3,198,752; 3,810,848; 3,989,762, among others.

Olefin hydration employing medium pore and large pore zeolite catalyst is a known synthesis method. As disclosed in U.S. Pat. No. 4,214,107 (Chang et al.), lower olefins, in particular propylene, are catalytically hydrated over a crystalline aluminosilicate zeolite catalyst having a silica to alumina ratio of at least 12 and a Constraint Index of from 1 to 12, e.g., acidic ZSM-5 type zeolite, to provide the corresponding alcohol, essentially free of ether and hydrocarbon by-product. Acid resin catalysts such as "Amberlyst 15" may also be used for hydration of light olefins.

The production of ether from secondary alcohols such as isopropanol and light olefins is known. As disclosed in U.S. Pat. No. 4,182,914, DIPE is produced from IPA and propylene in a series of operations employing a strongly acidic cationic exchange resin as catalyst. Recently, processes for the hydration of olefins to provide alcohols and ethers using zeolite catalyst such as ZSM-5 or zeolite Beta have been disclosed in U.S. Pat. Nos. 4,214,107 and 4,499,313 to Bell et al.; and U.S. Pat. Nos. 4,757,664, 4,857,664 and 4,906,187 to T. Huang. These patents are incorporated herein in their entirety by reference. One of the advantages in using zeolite catalyst for hydration and/or etherification of light olefins is the regenerability of the catalyst. Where resin based catalysts can decompose at the high temperatures required to remove deactivating amounts of carbonaceous deposits, zeolite catalysts remain thermally stable and can be regenerated oxidatively or in contact with hydrogen.

The hydration and etherification of lower olefins such as propylene to produce IPA and DIPE over a fixed bed of shape selective zeolite catalyst is generally carried out in liquid phase employing a feedstream comprising water and propylene at temperatures in excess of 200° F. and high pressure, preferably above 1000 psi (7000 kPa). While attempting to maximize the rate of conversion, process conditions are selected to also reduce the more disadvantageous reactions which can occur during the process that could compromise the process advantages. These adverse reactions include the oligomerization of propylene, the formation of deactivating amounts of coke and carbonaceous deposits on the catalyst and the hydrothermal attack of water on the catalyst. These adverse reactions tend to find favor with increasing temperature and concentration providing a challenging limit to workers in the field with respect to reactor temperature.

Conventional methods to convert propylene to DIPE involves isopropyl alcohol synthesis, and subsequent reaction of alcohol with additional propylene to give diisopropyl ether. Formation of the initial carbon-oxygen bond in an alcohol by olefin hydration, such as the formation of isopropanol by hydration of propene is a difficult step that puts severe demands on acid catalyst stability. These stability problems are due to hydrolysis of the active catalyst sites by liquid-phase water, and appear common to acidic resin, sulfuric acid, and zeolite catalysts. In the conversion of an IPA feedstream and a $C_3$ hydrocarbon feedstream comprising propene and propane to DIPE as conventionally practiced, the propylene conversion per pass is only about 20% or less. The reaction effluent is a mixture containing unreacted alcohol, propylene and propane, oligomeric hydrocarbon by-products, in addition to the DIPE product.

It is an objective of the present invention to provide a process for the conversion of propylene to diisopropyl ether or isopropanol with high selectivity.

A further objective of the invention is to provide a process for the conversion of propylene to diisopropyl ether or isopropanol with high selectivity by obviating the need to directly convert propylene to isopropanol by hydration of propylene with water.

Another object of he invention is to carry out the process using particularly selective shape selective zeolite catalysts, especially zeolite Beta.

SUMMARY OF THE INVENTION

A method has been discovered for the production of diisopropyl ether and isopropanol from propylene under conditions that reduce both the decomposition of isopropanol to propylene and water and the direct hydration of propylene with water to IPA. It has been found that when propylene hydration and etherification with IPA is carried out in the presence of zeolite Beta catalyst under conditions that are essentially starved with respect to available equivalents of water, the indirect hydration of propylene with IPA is favored and a single non-aqueous phase is more readily maintained that provides a high conversion of propylene to diisopropyl ether or isopropanol. The method involves a multistaged fixed bed liquid phase process wherein the necessary minimal conditions of water equivalents availability are established by interstage injection of a feedstream of appropriate composition. Either product DIPE or product IPA is recycled depending on whether the preferred product is DIPE or IPA.

In general, the invention comprises a multistaged fixed catalyst bed process for the production of diisopropyl ether and isopropanol comprising a fixed bed of serially connected stages containing zeolite Beta catalyst. A feedstream of propylene and water equivalents, wherein said water equivalents are selected from the group consisting of water, isopropanol and diisopropyl ether, is introduced into each stage at a rate sufficient to provide a mole ratio of water equivalents to propylene equivalents that increases in increments by stage from at least 0.1 in a first stage to at most 1.2 in a final stage. The feedstream is introduced at a temperature between 50 and 450° C., gauge pressure between 700 and 24000 kPa, and weight hourly space velocity between 0.10 and 30, based on catalyst, whereby a single non-aqueous liquid phase is maintained in the fixed bed. An effluent product stream is recovered comprising diisopropyl ether, isopropanol and water from the final stage. Isopropanol is recycled to the first stage when the preferred product is diisopropyl ether. When the preferred product is isopropanol, diisopropyl ether and water are recycled to the first stage.

More particularly, the invention comprises a serially connected multistaged fixed bed, single non-aqueous liquid phase, indirect propylene hydration process for the production of diisopropyl ether in contact with zeolite Beta catalyst. The process comprises introducing into a first serially connected fixed bed stage of the process a feedstream comprising propylene and an amount sufficient of water equivalents comprising isopropanol to provide a feedstream mole ratio of water equivalents to propylene equivalents between 0.1 and 0.45 in contact with the catalyst under etherification conditions at a pressure sufficient to maintain a single liquid hydrocarbon phase. Preferably, the feedstream contains more than 75 weight percent isopropanol and less than 25 weight percent water. Through this step a portion of the propylene is etherified with isopropanol to diisopropyl ether at a rate substantially faster than dehydration of isopropanol. Into each subsequent serially connected fixed bed stage of the process is introduced a feedstream comprising propylene, isopropanol and water in an amount sufficient to provide a mole ratio of water equivalents to propylene equivalents which is increased by stages from at least 0.5 to at most 1.2 over all of the subsequent stages. The propylene, isopropanol and water feedstream is in contact with the catalyst under etherification conditions at a pressure sufficient to maintain a single liquid hydrocarbon phase, whereby a portion of diisopropyl ether is converted to isopropanol in concert with the conversion of a portion of propylene to diisopropyl ether. From a final fixed bed stage of the process an effluent stream rich in diisopropyl ether is recovered comprising at least a 59 weight percent conversion of propylene to IPA and DIPE, wherein the effluent also contains isopropanol, propylene and water. The effluent stream is separated to recover the diisopropyl ether and recycle the isopropanol to the first stage. When the preferred product to be recovered from the process is isopropanol, DIPE and water are recycled to the first stage.

DETAILED DESCRIPTION OF THE INVENTION

The present invention teaches a method of producing DIPE and/or IPA from propylene in a multistaged catalytic process wherein the mole ratio of water equivalents to propylene injected with the feedstream to each stage of the multistage process is varied to maintain a single liquid hydrocarbon phase, also recited as a single liquid non-aqueous phase, and to promote those reactions in the overall process chemical equilibrium that ultimately favor selective as well as high conversion of propylene to DIPE or IPA. The foregoing ratio is described herein by repeatedly using a term "water equivalents".

The term "water equivalents" as used herein refers to the compounds present in the feed (oxygen containing compounds) that can react to produce water, i.e. are capable of yielding water under the conditions of the process. For example, a mole of propylene has a net water equivalency of zero; a mole of water has a net water equivalency of 1; a mole of isopropyl alcohol has a net water equivalency of 1 since one mole of IPA could dehydrate to produce one mole of water and one mole of propylene; a mole of diisopropyl ether has a net water equivalency of 1 since one mole of DIPE could dehydrate to produce one mole of water.

The term "propylene equivalents" refers to the compounds present in the process that can react to produce propylene, i.e. are capable of yielding propylene under the conditions of the process. For example, a mole of propylene has a net propylene equivalency of one; a mole of water has a net propylene equivalency of 0; a mole of isopropyl alcohol has a net propylene equivalency of 1 since one mole of IPA could dehydrate to produce one mole of water and one mole of propylene; a mole of diisopropyl ether has a net propylene equivalency of 2 since one mole of DIPE could dehydrate to produce two moles of propylene.

The term "mole ratio of water equivalents to propylene equivalents" as employed herein, is therefore a ratio in which the numerator is calculated from the mole fraction of water-yielding compounds in the feed while the denominator is the mole fraction of propylene-yielding compounds in the feed. The term mole ratio of water equivalents to propylene equivalents is referred to herein as Q.

As known in the art, the olefins hydration and etherification process is depicted in simplified form as comprising the reaction of propylene with water catalyzed by strong acid to form isopropanol. Reaction may be allowed to continue in the hydration zone to form di-isopropyl ether. The operating conditions of the olefin hydration and etherification reaction step include a temperature of about 50° to 450° C., preferably from 100° to 250° C. and most preferably from 120° to 220° C. The total pressure is about 700 to 24000 kPa (100 to about 3500 psi, preferably 500–2000 psi). Water to olefin reactant concentrations are maintained at mole ratio of about 0.1 to 30, preferably 0.1 to 5.

The preferred catalytic methods known in the art for making DIPE employ porous solid acid catalysts, such as zeolites Beta, Y, ZSM-35 and/or MCM-22 aluminosilicate. The preferred hydration/etherification catalyst comprises acidic, shape selective porous zeolite having a pore size of about 5–8 Angstroms, such as aluminosilicate zeolite Beta.

Also, MCM-22, is known for etherification catalysis, as disclosed by Marler et al. in U.S. Pat. No. 5,105,023.

DIPE etherification conditions may vary widely in choice of temperature, pressure and reaction time. The preferred method reacts propene with water in an adiabatic downflow reactor containing a fixed bed of catalyst, such as zeolite Beta, at 100° to 250° C. and pressure of at least 4000 kPa. However, it is understood that the unit operations described herein can be conducted with any number of specific process steps within the skill of the art.

The olefin hydration and etherification reaction step is carried out in liquid phase or supercritical dense phase in continuous manner using a fixed bed flow reactor. Weight hourly space velocity, based on catalyst weight is maintained in the range of 0.1 to 10/hour when operating continuously.

Various modifications can be made within the inventive concept, especially with regard to reactor system configuration. Although a single reactor bed may be employed, it is advantageous to employ a series of fixed bed reactor units to permit adequate control of reaction conditions, especially temperature, phase behavior and flow parameters. It is ordinarily desirable to recover any unreacted olefin and recycle it to the reactor. Unconverted isopropanol recovered from the final reactor effluent may also be recycled advantageously for further conversion to ether.

The reaction conditions of the present invention vary in some respects from the prior art, although the present process utilizes the same catalysts in an integrated, multistaged fixed bed reactor configuration. The preferred catalyst of the invention is zeolite Beta. The present process does not operate in a supercritical dense phase but in a single liquid hydrocarbon phase. The process of the invention is carried out at a temperature between 50° and 450° C., pressure between 700 and 24000 kPa, and weight hourly space velocity between 0.10 and 30, based on catalyst. Preferably, temperature is 160° C. pressure is 7000 kPa and weight hourly space velocity is 0.14.

The most significant differences of the process of the invention over the processes for propylene hydration and etherification known in the art relates to the content of the feed to the process and to the use of a multistage process with interstage injection of feed comprising a programmed ratio of water equivalent to propylene equivalents. The present invention introduces feedstreams comprising propylene equivalents and water equivalents (water, isopropanol and diisopropyl ether) into each stage of a multistage fixed bed reactor at a rate sufficient to provide a mole ratio of water equivalents to propylene equivalents that increases in increments by stage from at least 0.1 in a first stage to at most 1.2 in a final stage. Preferably, the process is carried out in four stages over zeolite Beta catalyst wherein the feedstream mole ratio of water equivalents to propylene equivalents is between 0.10 and 0.50 in a first stage bed, between 0.30 and 0.70 in a second stage bed, between 0.40 and 0.80 in a third stage bed, and between 0.50 to 1.2 in a final stage bed. Most preferably, the process is carried out in four stages over zeolite Beta catalyst wherein the feedstream mole ratio of water equivalents to propylene is between 0.40 and 0.50 in a first stage bed, between 0.50 and 0.70 in a second stage bed, between 0.70 and 0.80 in a third stage bed, and between 0.60 to 1.2 in a final stage bed.

Optionally in the invention, unconverted IPA is recycled to the first stage when the desired product is DIPE. When the preferred product is IPA, DIPE and water are recycled to the first stage reactor.

The present invention provides a zeolite based process that produces IPA from propylene and water based on an indirect route. Propylene first reacts with isopropanol to form DIPE. DIPE is then hydrated with water to form isopropanol. By this pathway, IPA is formed from propylene and water without directly reacting the two initial reagents. The indirect hydration route is possible due to the unique selectivities of shape selective zeolite catalyst systems. This selectivity is important in the DIPE system because propylene activation is the rate determining step. The fact that zeolites promote olefin reactions with alcohol and water greatly increases the efficiency of zeolites for propylene hydration and etherification. Indirect propylene hydration with isopropanol is maximized versus direct olefin hydration by reaction with water.

While zeolites are known to be highly selective for the condensation of secondary alcohols to form ether and water, the reverse reaction, water and ether yielding two alcohols, when coupled with zeolite-selective olefin etherification by an alcohol addition reaction, provides a route for propylene hydration that avoids the difficult reaction of propylene with water. In the propylene hydration system of the invention, water reacts with DIPE to form IPA. The IPA is then reacted with propylene to form more DIPE. Zeolites are significantly more selective for indirect hydration than classical liquid acids and sulfonated resins.

Indirect propylene hydration in the instant invention requires operation at water equivalents to propylene equivalents mole ratios (Q) below two in order to promote the reaction of propylene with IPA rather than water. Above a Q of 2, excess water assures that the direct hydration of propylene with water will predominate. Furthermore, the special selectivity of zeolite Beta requires running indirect propylene hydration in a single liquid hydrocarbon phase. The formation of separate aqueous or propylene vapor phases is highly undesirable and leads to catalyst aging. To avoid aqueous phase formation, reducing the amount of water and increasing the amount of IPA in the reactor is required. This situation promotes the reaction of propylene with IPA, one of the key reactions in the indirect hydration scheme.

Current, resin-catalyst, commercial propylene hydration processes operate with two phases (propylene vapor, water liquid) to prevent propylene oligomerization. However, the commercial resin catalyst system operates at Q's greater than 4 where two phases are present in the reactor (see, Direct Hydration of Propylene over Ion-Exchange Resins, J. R. Kaiser, Harold Beuther, L. D. More, and R. C. Odioso, I and EC Produce Res. & Dev., Vol 1, #4, December 1962, p. 296). Recently, a resin based DIPE process has also been commercialized which operates at low Q (0.5 to 2.0), but at temperatures and pressures selected to maintain two phases. Operating a propylene hydration system in a single, non-aqueous liquid phase is distinguished over these commercial operations. The finding that zeolites operate better in a non-aqueous liquid phase than in a mixed liquid/vapor system is completely unexpected according to the prior art. Published literature suggests (Kaiser et al., I and EC, Dec. 1962, p. 296 and U.S. Pat. No. 4,182,914 to Nippon Oil) that under non-aqueous liquid phase conditions, Amberlyst 15 produces more than 10 time more propylene oligomer than zeolites. Only the unique ability of zeolites to prevent propylene oligomerization allows non-aqueous liquid phase operation where the novel indirect propylene hydration route is possible.

Indirect hydration of propylene requires operation of propylene hydration under conditions that run counter to prior art. To achieve successful indirect hydration of propylene over zeolite Beta it has been discovered that low Q and one phase operation is preferred.

Reaction scheme 1 illustrates the proposed indirect hydration process in the DIPE/IPA system running in the IPA mode. Reaction (c) is the sum of reactions (a) and (b).

A similar scheme can be used for higher linear olefin feeds to produce the corresponding alcohol. Examples of higher linear olefins for the process include n-butenes, n-pentenes, 3-methyl-1-butene, n-hexenes, 3-methyl-1-pentene, 4-methyl-1-pentene, 4-methyl-2-pentene, 3,3-dimethyl-1-butene and the like.

Reaction scheme 2 illustrates the invention for the DIPE/IPA system in the DIPE mode. Reaction (c) in scheme 2 is the sum of reactions (a) and (b).

A similar scheme can be used for higher linear olefin feeds to produce the corresponding d-sec-alkyl- ethers.

A series of experiments were carried out to discover and demonstrate the novel conditions of the process of the present invention.

EXPERIMENT I

IPA Decomposition

An autoclave was loaded with 100 gm IPA and 0.5 gm catalyst. The autoclave was rapidly heated to reaction temperature (<1 min) and held for different contact times. When the target reaction time was reached, the autoclave was quenched in water. The entire reactor contents (gas and liquid) were analyzed. The total reactor content is given in Table 1.

EXPERIMENT II

The Reaction of DIPE with Water

A fixed bed unit was loaded with zeolite Beta catalyst. A 1:1 molar mixture of DIPE and water was allowed to flow through the reactor at a weight hourly space velocity based on catalyst (WHSV) of 74. The reactor pressure was held at 1000 psig (7000 kPa) and the temperature was brought up to 160° C. The product distribution is given in Table 2. An identical set of experiments was run except pure DIPE was fed to the reactor at a WHSV of 406 instead of DIPE and water. The results are also presented in Table 2.

EXPERIMENT III

Fixed Bed DIPE Experiments

The fixed bed experiments are reported in Table 3. The reactor pressure and temperature were 1000 psig and 320° F. (160° C.).

TABLE 1

| | | IPA REACTIONS[1] | | | | | |
|---|---|---|---|---|---|---|---|
| | | | Product (Wt %) | | | | |
| Catalyst[2] | T (°C.) | WHSV | $C_3^=$ | IPA | $H_2O$ | DIPE | $k_2/k_1$ |
| zeolite β | 100 | 2.2 | .054 | 98.7 | 0.20 | 1.03 | 4.0 |
| A-15[3] | 100 | 22 | 0.20 | 99.0 | 0.20 | 0.57 | 0.6 |
| ZSM-5 | 116 | 0.5 | 4 | 70 | 5 | 21 | 1.2 |
| zeolite β | 155 | 88.0 | 0.17 | 97.5 | 0.42 | 1.91 | 2.4 |
| A-15 | 160 | 2600 | 0.43 | 98.7 | 0.25 | 0.67 | 0.33 |
| ZSM-5 | 155 | 88.0 | .074 | 99.6 | 0.07 | .272 | 0.75 |

[1] 100 g IPA feed,
[2] 0.5 g catalyst,
[3] Amberlyst-15

Table 1 presents results for an investigation of the competitive reactions for the dehydration of one mole of isopropanol to a mole of propylene and a mole of water with a rate constant $k_{-1}$ and for the condensation of two moles of isopropanol to produce one mole of diisopropyl ether and one mole of water with a rate constant $k_2$.

At short contact times, the ratio of DIPE to propylene is related to the ratio of the rates of these two possible alcohol reactions ($k_2/k_{-1}$). From the ratios of $k_2/k_{-1}$ given in Table 1, the ratio of alcohol condensation to dehydration is 7 times higher for zeolite Beta than for Amberlyst 15 at a wide variety of temperatures. Over zeolite Beta, the reversible condensation reaction of IPA to DIPE and water is much faster than alcohol decomposition to propylene and water. This is not true for Amberlyst 15 or for classical acids (H. G. Karge, H. Kosters & Y. Wada, "Dehydration of Cyclohexanol as a Test Reaction of Zeolite Activity", Proc. 5th. Symp. on Zeolites, p. 308, 1982; A. Streitweiser and C. Heathcock, Introduction to Organic Chemistry, Macmillan Publishing Co., 1976, p. 237; Wagner & Zook, Synthetic Organic Chemistry, Wiley, p. 355.).

TABLE 2

| | | | Product Composition (wt %) | | | | |
|---|---|---|---|---|---|---|---|
| Feed DIPE | (mol %) H$_2$O | DIPE Conv, % | Propylene | H$_2$O | IPA | DIPE | Mol IPA/ Mol Propylene |
| 100 | 0 | 7.4 | 4.0 | 0.2 | 2.6 | 92.6 | 0.5 |
| 50 | 50 | 5.0 | 0.5 | 16.2 | 2.2 | 81.0 | 3.4 |

DIPE + Water Reactions

Table 2 contains data from the competitive reactions of one mole of DIPE to produce one mole of propylene and one mole of isopropanol and the reaction of one mole of DIPE and one mole of water to produce two moles of isopropanol over zeolite Beta.

The data in Table 2 compare the product selectivities at low conversions for the hydration reaction of DIPE to form IPA vs. DIPE decomposition to propylene and IPA. When pure DIPE is fed, propylene is the major product. The mole ratio of IPA: propylene in the product was 0.5 with between 0 and 0 wt % conversion. When an equimolar amount of water is cofed, IPA is the dominant reaction product. The mole ratio of IPA to propylene is 3.4 in this product, an almost sevenfold increase when compared with pure DIPE ($k_2$) feed. This set of experiments clearly show that DIPE hydration is faster than DIPE decomposition in a 1:1 molar water:DIPE feed.

Additional evidence for rapid DIPE hydration to IPA is provided in Table 4. In these experiments, replacing two-thirds of the IPA in an IPA/propylene feed with the stoichiometric equivalent amount of DIPE and water leads to the same product distribution.

The results presented in Table 3 demonstrate that by using zeolite Beta, the rate of propylene conversion to oxygenates (DIPE and IPA) increases as the reaction mixture approaches equilibrium. In the first set of experiments, with water and propylene feed, a WHSV of 5 was required at 162° C. to consume 5.1 wt % propylene. In the second set of experiments, the feed was much closer to equilibrium (equilibrium composition is listed in Table 3 for comparison) and contained IPA and DIPE in addition to water and propylene. In this case, despite being closer to equilibrium, about twice as much propylene was consumed at an even higher weight hourly space velocity (WHSV) of 8. The fact that propylene conversion increases as equilibrium is approached (Table 3), in concert with the selectivity for DIPE hydration shown in Table 2, demonstrates that the indirect hydration pathway (i.e. water reacts with DIPE vs. with propylene) becomes significant as DIPE concentration builds.

Figure 1:
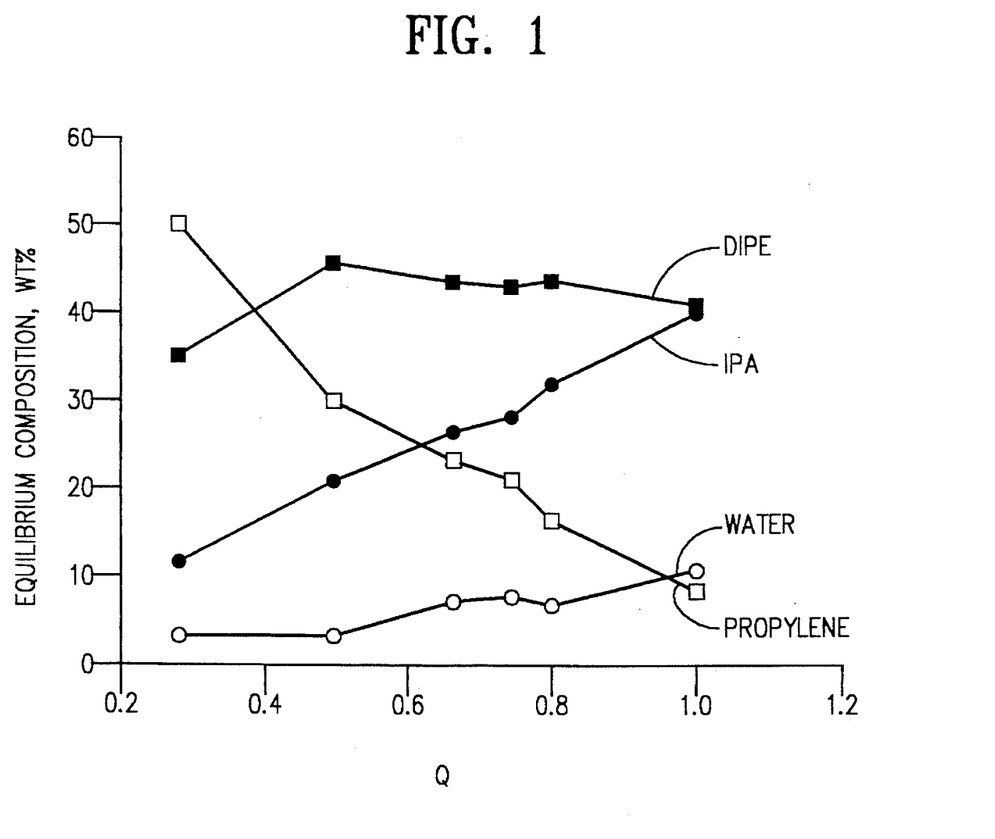
FIG. 1 is a graph illustrating the relationship between the equilibrium concentration of diisopropyl ether versus (Q) the mole ratio of water equivalents to propylene equivalents for the process.

All propylene hydration or etherification processes must overcome a number of challenges inherent to the system. All the reactions in the propylene hydration network that interconvert IPA, DIPE, water and propylene are reversible, so all species are reactive and present at all times. The amount of each component present at equilibrium depends on Q. FIG.

TABLE 3

Propylene Reactions[1]

| | WHSV | Propylene | IPA | H$_2$O | DIPE | $C_3$ = consumed Wt % |
|---|---|---|---|---|---|---|
| Equilibrium | N/A | 30 | 18 | 3.0 | 49 | N/A |
| Feed | | 70 | 0 | 30 | 0 | |
| zeolite β | 5 | 64.9 | 6.8 | 27 | 1.2 | 5.1 |
| Feed | | 43 | 19 | 5.0 | 34 | |
| zeolite β | 8 | 33 | 21 | 3.0 | 43 | 10.0 |

Weight %

[1]Q = 0.5 and
T = 162° C. in all cases

TABLE 4

Neat IPA versus IPA/DIPE/Water Recycle[1]

| | Propylene | water | IPA | DIPE | Dimer |
|---|---|---|---|---|---|
| Feed | 39.9 | — | 60.1 | — | — |
| Product | 29.9 | 4.3 | 20.8 | 41.9 | 0.5 |
| Feed | 41.9 | 6.0 | 19.5 | 32.5 | — |
| Product | 32.4 | 3.1 | 22.4 | 43.8 | 0.7 |

[1]Q = 0.5,
T = 162° C.,
P = 7000 Kpa,
WHSV = 2.0

1 plots the equilibrium concentration of each species at 1000 psig and 320° F. for various Q values between 1 and 0.1.

A second major challenge facing all propylene hydration schemes is deciding how to mix propylene and water. Propylene is a non-polar gas, while water is a polar liquid. The mixed system is non-ideal and under commercial hydration systems is a mixture of one or more of the following possible phases: gas phase, supercritical phase, aqueous phase, and liquid hydrocarbon phase. One of the most basic decisions in a design is deciding in what phase or phases to operate. When mixed phases are chosen, it is important to maintain the mixed phases characteristics of the system throughout the reactor section. When single phase operation is chosen, it is equally important to prevent multiple phase formation during the course of the reaction.

A relationship exists between multiphase formation and Q. At high Q, aqueous phase formation is unavoidable and at low Q vapor phase formation is unavoidable. At a Q of 0.75, 320° F. (162° C.) and 1000 PSIG (7000 kPa), the equilibrium product is approximately equimolar in DIPE and IPA, and the feedstock is exactly stoichiometric for this product mixture. At this equilibrium composition, as shown in FIG. (1), the mole percent of propylene is equal to the mole percent of water. This is an ideal situation for maintaining a single liquid hydrocarbon phase because there is sufficient IPA to prevent aqueous phase formation, sufficient IPA and DIPE to dissolve the propylene, and an equal amount of water and propylene to bring together into a single phase. As Q is dropped from 0.75, higher pressure is needed to compress/dissolve the increased amount of propylene into a reduced amount of total liquid products. In addition, as Q drops, increased propylene is offset by decreased IPA while DIPE composition remains the same. IPA is an excellent cosolvent and is needed to prevent aqueous phase formation. So as Q drops, less water is tolerated by the system before aqueous phase formation.

The following approaches have been designed to meet the challenge of maintaining a single liquid hydrocarbon phase while minimizing losses in activity, stability, and selectivity. The processes are designed to run above a Q of 0.4 where 1000 psig is sufficient to maintain a single liquid hydrocarbon phase.

Experiments have been conducted in the lab which demonstrate the feasibility of a process design (FIG. 2) which involves feeding propylene into the first bed of a 4 bed reactor along with recycled IPA (201) at a Q of 0.49. In between stages, water is injected (202, 203, 204) to raise Q so that the effluent (204) leaving the final reactor is at a Q of 0.92. Without optimization, this process design provided an overall propylene conversion per pass of 59% at 320° F. (160° C.) 1000 psi (7000 kPa) and a total WHSV (on zeolite) of 0.14 and has the following advantages:

Operating at the lowest possible Q maximizes reaction rates by (a) minimizing competitive adsorption by water and (b) maintaining selectivity for indirect (vs. direct) propylene hydration.

A single liquid hydrocarbon phase is maintained by not adding water until after IPA and DIPE build up. IPA serves as a cosolvent, and DIPE dehydrates the reaction mixture by reacting with water to form IPA.

High single pass conversions of both propylene and water are obtained by increasing Q.

Figure 2:
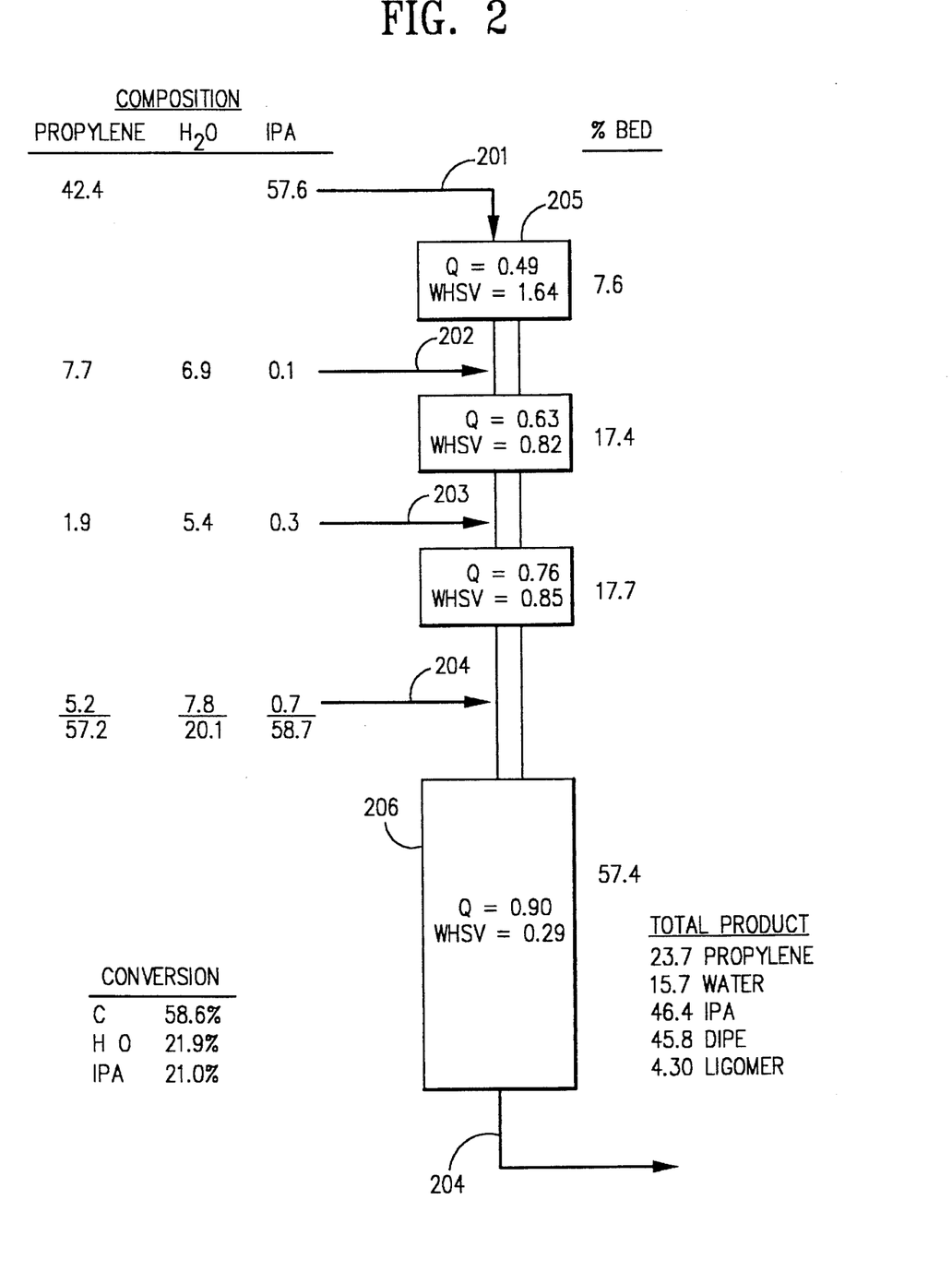
FIG. 2 is a flow diagram for a preferred 4 stage fixed bed mode of the process of the invention.

Operating across the range of Q's is a desirable compromise that improves activity while maintaining high conversion. Reactor bed 205 operates at Q=0.48 where catalyst activity is higher but equilibrium conversion is lower. Reactor bed 206 operates at Q=0.92 where equilibrium conversion is higher but catalyst is lower.

Starting at low Q allows product (IPA and DIPE) recycle ratios of less than 1.

Flexible production of DIPE or IPA is possible.

Although the demonstration run started at a Q of 0.49 and ended at a Q of 0.92, zeolite Beta maintains selectivity and activity between Q of 0.28 and 1.0.

Figure 3:
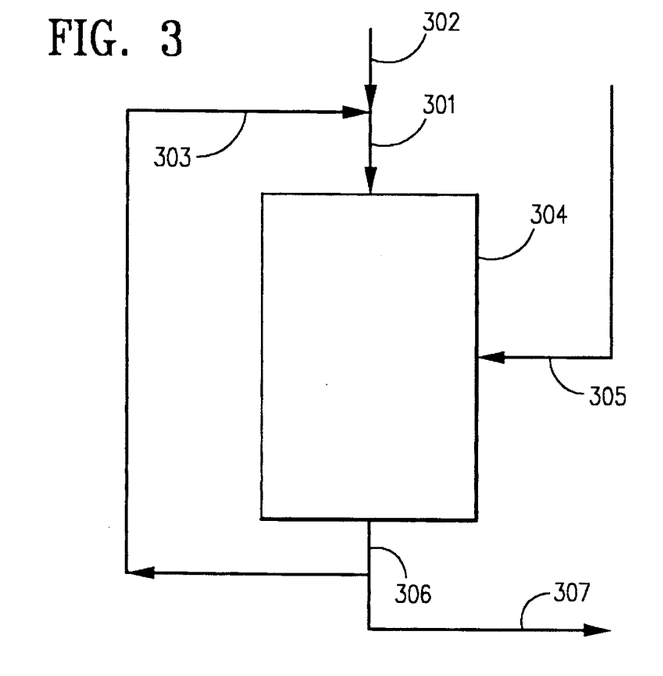
FIG. 3 shows a reactant/product flow diagram for an interstage injection process designed to produce DIPE alone.

FIG. 3 shows a reactant/product flow diagram for an interstage water injection multistage fixed bed process employing zeolite Beta catalyst and designed to produce DIPE alone. The single pass propylene design leads to 69% propylene conversion to DIPE. The IPA formed is recycled to balance the process.

Referring to FIG. 3, a feedstream 301 comprising 76.5 lbs of propylene 302 and 47.1 lbs of recycled IPA 303 at a Q of 0.4 is passed to the multistaged reactor 304 in conjunction with 23.5 lbs of water 305. The reactor effluent 306 has a Q of 0.8. The product stream 307 comprises 64.2 lbs of DIPE, 11.8 lbs of water and 24.0 lbs of propylene.

Figure 4:
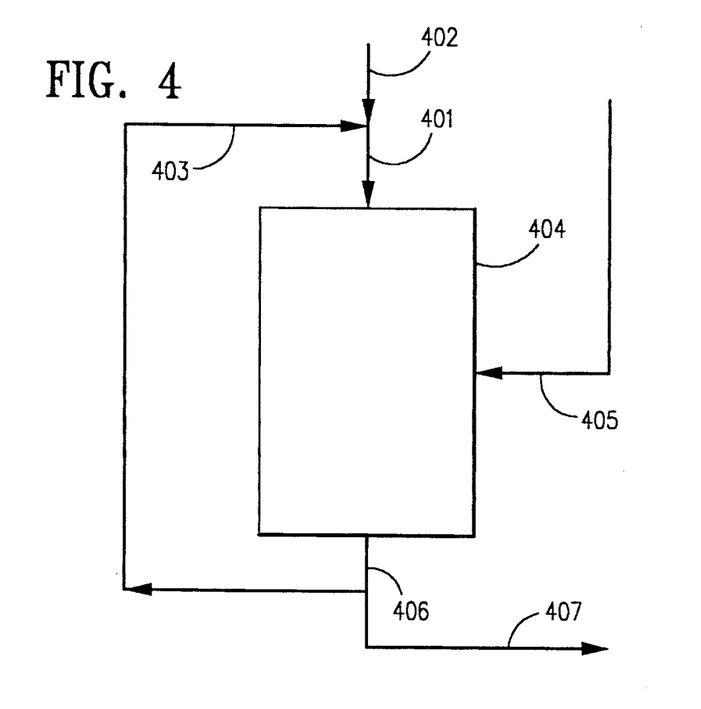
FIG. 4 shows a reactant/product flow diagram for an interstage injection process designed to produce IPA alone.

FIG. 4 shows a reactant/product flow diagram for an interstage water injection process designed to produce IPA. This analogous single pass propylene design will lead to an 87% conversion of propylene to IPA. The DIPE formed is recycled to balance the process.

Referring to FIG. 4, a feedstream 401 comprising 38.0 lbs of propylene 402 and 35.5 lbs of recycled DIPE plus 6.3 lbs of water 403 at a Q of 0.44 is passed to the multistaged reactor 304 in conjunction with 20.2 lbs of water 405. The reactor effluent 406 has a Q of 1.2. The product stream 407 comprises 47.0 lbs of IPA, 12.5 lbs of water and 5.0 lbs of propylene.

Since DIPE reacts quickly with water to form IPA, recycling one mole of water and one mole of DIPE is equivalent to recycling two moles of IPA. This is illustrated clearly in Table 4 which shows that replacing two thirds of the moles of IPA with the stoichiometric equivalent amount of DIPE and water leads to the same product distribution.

The flexibility of the zeolite Beta propylene hydration process is significantly constrained by the necessity of preventing the formation of an aqueous phase. IPA to water weight ratio in the reactor must remain above 2 to prevent aqueous phase formation. Therefore, it is not possible to feed water and propylene alone, and recycle becomes a necessity.

At high pressure and low Q where no aqueous phase exists, zeolite Beta is stable and highly active for IPA/DIPE synthesis from propylene and water with good selectivity and high equilibrium propylene conversion. This combination of desirable process targets can only be achieved by a catalyst that remains active and selective in a single liquid hydrocarbon phase reaction mixture. Other catalysts such as Amberlyst 15 require two phases (high Q at high pressure) to maintain good selectivity. This leads to large increases in operating costs due to large excesses of water. Zeolite Beta is the only catalyst demonstrated to remain active and selective in a single liquid hydrocarbon phase at high pressure and low Q.

Based on the unique activity and selectivity of zeolite Beta, the novel process designs of the invention incorporating interstage water or interstage water and propylene injection can reduce the capital and utility requirements for DIPE and IPA synthesis. Interstage water and propylene injection provides the ability to achieve high single pass conversion of propylene at a reasonable WHSV. The overall process can be balanced with either mostly IPA recycle (DIPE production mode) or mostly DIPE recycle (IPA production mode).

What is claimed is:

1. A multistaged fixed catalyst bed process for the production of diisopropyl ether and isopropanol comprising:

providing said fixed bed comprising serially connected stages containing zeolite Beta catalyst;

introducing a feedstream comprising propylene and water equivalents, wherein said water equivalents are selected from the group consisting of water, isopropanol and diisopropyl ether, into each stage at a rate sufficient to provide a mole ratio of water equivalents to propylene equivalents that increases in increments by stage from at least 0.1 in a first stage to at most 1.2 in a final stage, wherein said feedstream is introduced at a temperature between 50° and 450° C., pressure between 700 and 24000 kPa, and weight hourly space velocity between 0.10 and 30, based on catalyst, whereby a single non-aqueous liquid phase is maintained in said fixed bed; and recovering an effluent product stream comprising diisopropyl ether, isopropanol and water from said final stage.

2. The process of claim 1 further comprising separating said product stream and recycling isopropanol from said product stream whereby the production of diisopropyl ether is enhanced.

3. The process of claim 1 further comprising separating said product stream and recycling diisopropyl ether and water from said product stream whereby the production of isopropanol is enhanced.

4. The process of claim 2 wherein said multistaged fixed bed comprises said first stage, a second stage, a third stage and said final stage wherein said feedstream mole ratio of water equivalents to propylene equivalents is between 0.10 and 0.50 in said first stage bed, between 0.30 and 0.70 in said second stage bed, between 0.40 and 0.80 in said third stage bed, and between 0.50 to 1.2 in said final stage, wherein the temperature is 160° C., pressure is 7000 kPa and weight hourly space velocity is 0.14, whereby at least a 59 weight percent conversion of propylene to diisopropyl ether plus isopropanol is achieved.

5. The process of claim 3 wherein said multistaged fixed bed comprises said first stage, a second stage, a third stage and said final stage wherein said feedstream mole ratio of water equivalents to propylene equivalents is between 0.40 and 0.50 in said first stage bed, between 0.50 and 0.70 in said second stage bed, between 0.70 and 0.80 in said third stage bed, and between 0.60 to 1.2 in said final stage, wherein the temperature is 160° C., pressure is 7000 kPa and weight hourly space velocity is 0.14, whereby at least an 87 weight percent conversion of propylene to isopropanol plus diisopropyl ether is achieved.

6. A serially connected multistaged fixed bed, single non-aqueous liquid phase, indirect propylene hydration process for the production of diisopropyl ether in contact with zeolite Beta catalyst, said process comprising:

introducing into a first serially connected fixed bed stage of the process a feedstream comprising propylene and an amount sufficient of water equivalents comprising isopropanol to provide a feedstream mole ratio of water equivalents to propylene equivalents between 0.1 and 0.5 in contact with said catalyst under etherification conditions at a pressure sufficient to maintain said liquid phase, whereby a portion of said propylene is etherified with said isopropanol to diisopropyl ether at a rate substantially faster than dehydration of said isopropanol;

introducing into each subsequent serially connected fixed bed stage of the process a feedstream comprising propylene, isopropanol and water in an amount sufficient to provide a mole ratio of water equivalents to propylene equivalents which is increased by stages from at least 0.5 to at most 1.2 over all of said subsequent stages, wherein said propylene, isopropanol and water feedstream is in contact with said catalyst under etherification conditions at a pressure sufficient to maintain said liquid phase, whereby a portion of said diisopropyl ether is converted to isopropanol in concert with the conversion of a portion of said propylene to diisopropyl ether;

recovering from a final fixed bed stage of the process an effluent stream rich in diisopropyl ether comprising at least a 59 weight % conversion of propylene to said ether, wherein said effluent also contains isopropanol, propylene and water; and separating said effluent stream to recover said diisopropyl ether and recycle the isopropanol to the first stage.

7. The process of claim 6 wherein said etherification conditions comprise temperature between 50° and 450° C., pressure between 700 and 24000 kPa, and weight hourly space velocity between 0.10 and 30, based on catalyst.

8. The process of claim 7 wherein said etherification conditions comprise temperature between 150° and 200° C., pressure between 5600 kPa and 8400 kPa and weight hourly space velocity between 0.10 and 2.

9. The process of claim 8 wherein the temperature is 160° C., pressure is 7000 kPa and weight hourly space velocity is 0.14.

10. The process of claim 9 wherein said multistaged fixed bed comprises said first stage, a second stage, a third stage and said final stage wherein said feedstream mole ratio of water equivalents to propylene equivalents is between 0.40 and 0.50 in said first stage bed, between 0.50 and 0.70 in said second stage bed, between 0.70 and 0.80 in said third stage bed, and between 0.60 to 1.2 in said final stage.

11. The process of claim 10 wherein said first stage weight hourly space velocity is between 1.5 and 2.0, between 0.5 and 1.0 in said second and third stages, and between 0.10 and 0.50 in said final stage.

12. A serially connected multistaged fixed bed, single non-aqueous liquid phase, propylene hydration process for the production of isopropanol in contact with zeolite Beta catalyst, said process comprising:

introducing into a first serially connected fixed bed stage of the process a feedstream comprising propylene and an amount sufficient of water equivalents comprising diisopropyl ether and water to provide a feedstream mole ratio of water equivalents to propylene equivalents between 0.1 and 0.45 in contact with said catalyst under propylene hydration conditions at a pressure sufficient to maintain said liquid phase, whereby a portion of said diisopropyl ether is converted to said isopropanol;

introducing into each subsequent serially connected fixed bed stage of the process a feedstream comprising propylene equivalents and water in an amount sufficient to provide a mole ratio of water equivalents to propylene which is increased by stages from at least 0.5 to at most 1.2 over all of said subsequent stages, wherein said propylene and water feedstream is in contact with said catalyst under propylene hydration conditions at a pressure sufficient to maintain said liquid phase;

recovering from a final fixed bed stage of the process an effluent stream rich in isopropanol comprising at least a 87 weight percent conversion of propylene to isopropanol wherein said effluent also contains diisopropyl ether, propylene and water; and separating said effluent stream to recover said isopropanol and recycle the diisopropyl ether and water to the first stage.

13. The process of claim 12 wherein said propylene hydration conditions comprise temperature between 50° and 450° C., pressure between 700 and 24000 kPa, and weight hourly space velocity between 0.10 and 30, based on catalyst.

14. The process of claim 13 wherein said etherification conditions comprise temperature between 150° and 200° C., pressure between 5600 kPa and 8400 kPa and weight hourly space velocity between 0.10 and 2.

15. The process of claim 14 wherein the temperature is 160° C., pressure is 7000 kPa and weight hourly space velocity is 0.14.

16. The process of claim 15 wherein said multistaged fixed bed comprises said first stage, a second stage, a third stage and said final stage wherein said feedstream mole ratio of water equivalents to propylene equivalents is between 0.40 and 0.50 in said first stage bed, between 0.50 and 0.70 in said second stage bed, between 0.70 and 0.80 in said third stage bed, and between 0.60 to 1.2 in said final stage.

17. The process of claim 16 wherein said first stage weight hourly space velocity is between 1.5 and 2.0, between 0.5 and 1.0 in said second and third stages, and between 0.10 and 0.50 in said final stage.

* * * * *

UNITED STATES PATENT AND TRADEMARK OFFICE
CERTIFICATE OF CORRECTION

PATENT NO. : 5,569,789
DATED : October 29, 1996
INVENTOR(S) : Weldon K. Bell et al.

It is certified that error appears in the above-indentified patent and that said Letters Patent is hereby corrected as shown below:

Column 14, line 41, after "propylene" insert --equivalents--.

Signed and Sealed this

Twenty-eighth Day of January, 1997

Attest:

BRUCE LEHMAN

Attesting Officer    Commissioner of Patents and Trademarks